(12) United States Patent
Kitagawa et al.

(10) Patent No.: US 9,213,041 B2
(45) Date of Patent: Dec. 15, 2015

(54) RACK TRANSPORTING APPARATUS AND SAMPLE PROCESSING APPARATUS

(75) Inventors: Nobuhiro Kitagawa, Akashi (JP); Kei Takai, Kobe (JP); Hiroo Tatsutani, Kobe (JP)

(73) Assignee: SYSMEX CORPORATION, Kobe-Shi (JP)

(*) Notice: Subject to any disclaimer, the term of this patent is extended or adjusted under 35 U.S.C. 154(b) by 0 days.

(21) Appl. No.: 12/883,607

(22) Filed: Sep. 16, 2010

(65) Prior Publication Data

US 2011/0076193 A1    Mar. 31, 2011

(30) Foreign Application Priority Data

Sep. 30, 2009  (JP) .................. 2009-228311

(51) Int. Cl.
| | |
|---|---|
| *G01N 35/00* | (2006.01) |
| *G01N 35/02* | (2006.01) |
| *G01N 35/04* | (2006.01) |
| *G01N 35/10* | (2006.01) |
| *G01N 31/00* | (2006.01) |
| *G01N 33/48* | (2006.01) |

(52) U.S. Cl.
CPC .............. *G01N 35/026* (2013.01); *G01N 35/02* (2013.01); *G01N 35/04* (2013.01); *G01N 35/10* (2013.01); *G01N 35/1011* (2013.01); *G01N 35/1065* (2013.01); *G01N 35/1081* (2013.01); *G01N 2035/0401* (2013.01); *G01N 2035/0412* (2013.01); *G01N 2035/0415* (2013.01); *G01N 2035/0424* (2013.01); *G01N 2035/0465* (2013.01)

(58) Field of Classification Search
CPC .............. G01N 2035/0415; G01N 2035/0401; G01N 2035/0412; G01N 2035/0465; G01N 2035/0424; G01N 35/026; G01N 35/0092; G01N 35/02; G01N 35/04; G01N 35/10; G01N 35/1011; G01N 35/1065
See application file for complete search history.

(56) References Cited

U.S. PATENT DOCUMENTS

| | | | |
|---|---|---|---|
| 2002/0098596 A1* | 7/2002 | Matsubara et al. | 436/501 |
| 2003/0235514 A1 | 12/2003 | Nogawa et al. | |
| 2006/0216199 A1* | 9/2006 | Koike | 422/65 |
| 2007/0202011 A1* | 8/2007 | Nogawa et al. | 422/65 |
| 2007/0207056 A1* | 9/2007 | Veiner et al. | 422/63 |

FOREIGN PATENT DOCUMENTS

| | | |
|---|---|---|
| JP | 62-218870 A | 9/1987 |
| JP | 06-034642 A | 2/1994 |

(Continued)

*Primary Examiner* — Lyle Alexander
*Assistant Examiner* — Jennifer Wecker
(74) *Attorney, Agent, or Firm* — Brinks Gilson & Lione

(57) ABSTRACT

A rack transporting apparatus including: a first transport path for transporting a sample rack to the sample processing unit; a second transport path for transporting the sample rack, without passing through the sample processing unit, in the same direction as a transport direction of the sample rack by the first transport path; a third transport path for transporting the sample rack in the opposite direction of the transport direction by the first transport path and the second transport path; a first rack transferring mechanism for transferring the sample rack from the second transport path to the first transport path through a first holding region being capable of holding the sample rack; and a second rack transferring mechanism for transferring the sample rack from the first transport path to the second transport path or the third transport path through a second holding region being capable of holding the sample rack.

21 Claims, 13 Drawing Sheets

(56) References Cited

FOREIGN PATENT DOCUMENTS

| | | | |
|---|---|---|---|
| JP | 11-271316 A | | 10/1999 |
| JP | 2003-344423 A | | 12/2003 |
| JP | 2007309743 A | * | 11/2007 |
| JP | 2008-032652 A | | 2/2008 |
| JP | 2008032652 A | * | 2/2008 |

* cited by examiner

RACK TRANSPORTING APPARATUS AND SAMPLE PROCESSING APPARATUS

RELATED APPLICATIONS

This application claims priority under 35 U.S.C. §119 to Japanese Patent Application No. 2009-228311 filed on Sep. 30, 2009, the entire content of which is hereby incorporated by reference.

BACKGROUND OF THE INVENTION

1. Field of the Invention

The present invention relates to a rack transporting apparatus for transporting a sample rack holding sample containers, and a sample processing apparatus in which the rack transporting apparatus is used.

2. Description of the Related Art

Japanese Patent Publication No. 2008-32652 discloses a conventional transporting apparatus for transporting a sample rack to a sample processing unit which processes a sample.

Japanese Patent Publication No. 2008-32652 discloses a transporting apparatus disposed along an arrangement direction of a plurality of analyzing units disposed in a linear arrangement, wherein the transporting apparatus transports a sample rack, delivered by a rack delivering unit, to a sample suctioning position of the analyzing units and then finally send back the sample rack to a rack collecting unit disposed on the same side of the rack delivering unit relative to the analyzing units. The transporting apparatus is equipped with an overtake lane where a sample rack for urgent sample and a sample rack for interrupt sample are transported, an ordinary lane where a sample rack for general sample is transported, and a return lane where a sample rack from which a sample has been suctioned is transported back to a rack collecting unit, wherein the ordinary lane is provided with sample suctioning positions of the analyzing units. The transporting apparatus further has a lane changer which changes the lane to be selected for transporting the sample rack. The lane changer which is slidable in a direction orthogonal to a transport direction of the sample rack can transfer the sample rack from the overtake lane to the ordinary lane and from the ordinary lane to the return lane.

According to the transporting apparatus recited in Japanese Patent Publication No. 2008-32652, however, the sample rack on the overtake lane has to stay there until the lane changer is ready to transfer the sample rack on the overtake lane to the ordinary lane when the transfer of the sample rack to the ordinary lane is prevented by, for example, the presence of any other sample rack on the ordinary lane. In the event that the sample rack on the ordinary lane cannot be transferred to the return lane by, for example, the presence of any other sample rack on the return lane, the sample rack on the ordinary lane is kept there until the sample rack on the ordinary lane can be transferred to the return lane by the lane changer. Therefore, when trying to transfer any subsequent rack using the overtake lane or the ordinary lane during the occurrence of these events, the transport of the subsequent rack on the overtake lane or the ordinary lane is temporarily stopped. Thus, it fails to smoothly transfer the subsequent sample rack using the overtake lane or the ordinary lane.

SUMMARY OF THE INVENTION

The scope of the present invention is defined solely by the appended claims, and is not affected to any degree by the statements within this summary.

A first aspect of the present invention is a rack transporting apparatus for transporting a sample rack to a sample processing unit which processes a sample, comprising: a first transport path for transporting a sample rack holding a sample container containing a sample to the sample processing unit; a second transport path for transporting the sample rack, without passing through the sample processing unit, in the same direction as a transport direction of the sample rack by the first transport path; a third transport path for transporting the sample rack in the opposite direction of the transport direction by the first transport path and the second transport path; a first rack transferring mechanism for transferring the sample rack from the second transport path to the first transport path through a first holding region being capable of holding the sample rack; and a second rack transferring mechanism for transferring the sample rack from the first transport path to the second transport path or the third transport path through a second holding region being capable of holding the sample rack.

A second aspect of the present invention is a sample processing apparatus, comprising: a rack transport unit for transporting a sample rack holding a sample container containing a sample; and a sample processing unit for processing the sample in the sample rack transported by the rack transport unit, wherein the rack transport unit comprises: a first transport path for transporting the sample rack to the sample processing unit; a second transport path for transporting the sample rack, without passing through the sample processing unit, in the same direction as a transport direction of the sample rack by the first transport path; a third transport path for transporting the sample rack in the opposite direction of the transport direction by the first transport path and the second transport path; a first rack transferring mechanism for transferring the sample rack from the second transport path to the first transport path through a first holding region being capable of holding the sample rack; and a second rack transferring mechanism for transferring the sample rack from the first transport path to the second transport path or the third transport path through a second holding region being capable of holding the sample rack.

DETAILED DESCRIPTION OF THE EMBODIMENT

Figure 1:
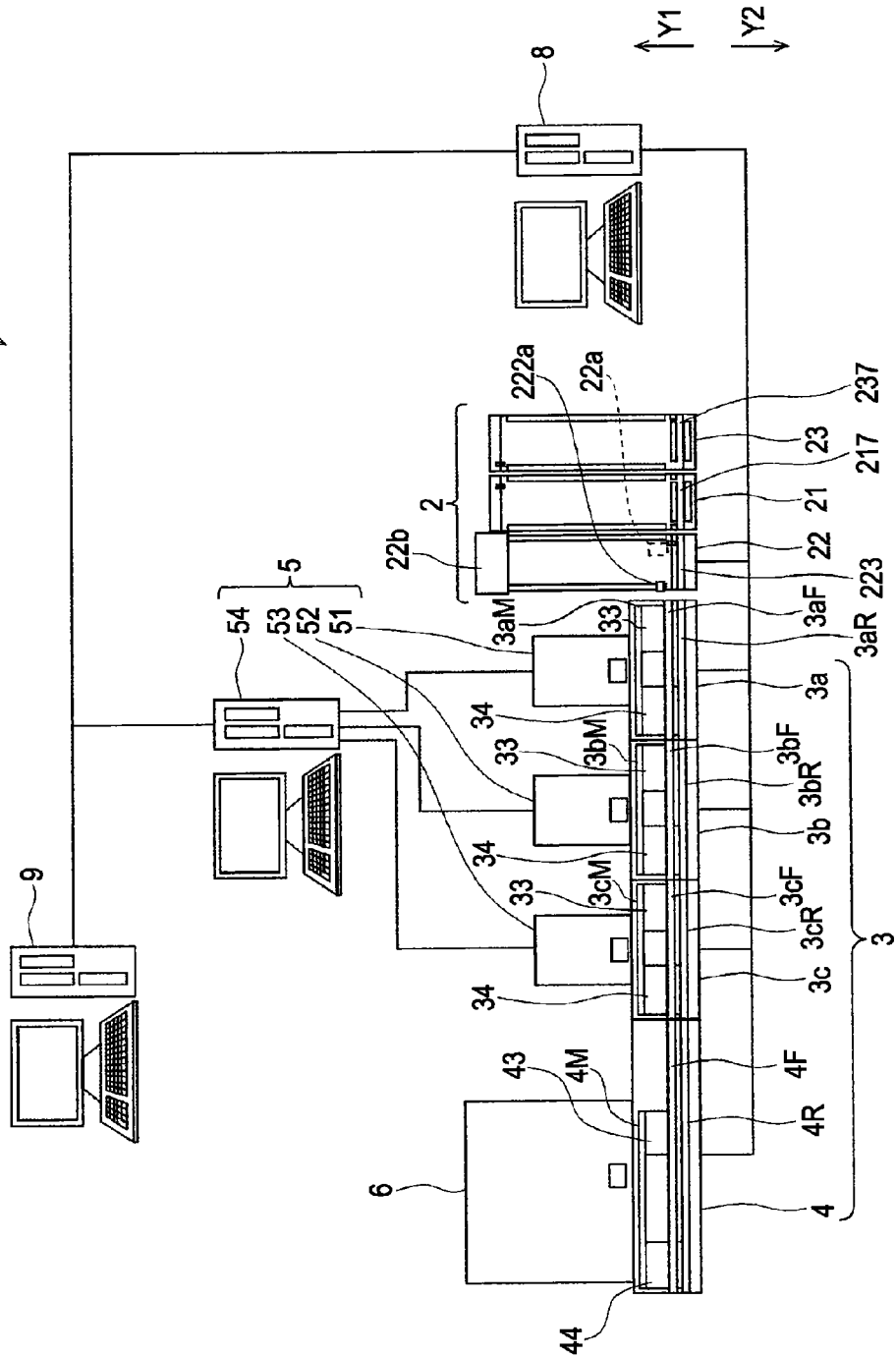
FIG. 1 is a schematic plan view illustrating a whole structure of a sample processing apparatus according to an embodiment of the present invention.

A preferred embodiment of the present invention is described below referring to the drawings.

[Structure of Sample Processing Apparatus]

FIG. 1 is a schematic plan view illustrating a whole structure of a sample processing apparatus equipped with a transport device according to the embodiment. As illustrated in FIG. 1, a sample processing apparatus 1 has a sample feed and collection device 2, a sample transport device 3, a hemocyte analyzing device 5, a smear preparation device 6, and a system control device 8. The sample processing apparatus 1 according to the present embodiment is connected to a test information management device 9 through a communication network to allow communication therebetween.

The sample transport device 3 has sample transport units 3a, 3b, 3c, and 4, and these sample transport units 3a, 3b, 3c, and 4 are serially connected to one another so as to linearly extend in lateral directions of the drawing. The hemocyte analyzing device 5 has three measurement units 51, 52, and 53, and an information processing unit 54. The measurement unit 51 is provided behind the sample transport unit 3a, the measurement unit 52 is provided behind the sample transport unit 3b, and the measurement unit 53 is provided behind the sample transport unit 3c. The smear preparation device 6 is provided behind the sample transport unit 4.

The sample transport units 3a, 3b, 3c, and 4 are respectively provided with measurement lines 3aM, 3bM, and 3cM, and a processing line 4M (first transport path) for transporting a sample rack L so that samples are supplied to the measurement units 51, 52, and 53, and the smear preparation device 6, which are all laterally extending. The sample transport device 3 is further provided with transport lines 3aF, 3bF, 3cF, and 4F (second transport path) laterally disposed in a linear manner in the sample transport units 3a, 3b, 3c, and 4 for transporting a sample rack holding a plurality of samples leftward in the drawing, and return lines 3aR, 3bR, 3cR, and 4R (third transport path) disposed in parallel with the transport lines 3aF, 3bF, 3cF, and 4F for transporting the sample rack rightward in the drawing. Between the transport lines 3aF, 3bF, 3cF, and 4F and the measurement lines 3aM, 3bM, and 3cM and the processing line 4M, there are pre-analysis rack holding sections 33 and 43 (first holding region) serving as transport paths for transporting the sample rack from the transport line to a starting point of the measurement line (processing line) and also as regions for holding the sample rack, and post-analysis rack holding sections 34 and 44 (second holding region) which are transport paths for transporting the sample rack from a terminal point of the measurement line (processing line) to the transport line or the return line and also regions for retaining the sample rack.

The sample feed and collection device 2 that can feed the sample rack is connected to the right end of the sample transport device 3. The sample rack carried out of the sample feed and collection device 2 is transported by the transport line 3aF, 3bF, 3cF or 4F of the sample transport device 3. The sample rack is transported from the transport line 3aF, 3bF, 3cF or 4F to the measurement line 3aM, 3bM, 3cM or processing line 4M by way of the pre-analysis rack holding section 33 or pre-process rack holding section 43 of the sample transport unit 3a, 3b, 3c, or 4 corresponding to the measurement unit 51, 52, 53, or smear preparation device 6 which is a transport destination, and then transported on the measurement line or the processing line to be supplied to its transport destination, the measurement unit 51, 52, 53, or smear preparation device 6. After the sample is supplied to the measurement 51, 52, 53, or smear preparation device 6, the sample rack L is transferred from the measurement line 3aM, 3bM, 3cM, or processing line 4M to the return line 3aR, 3bR, 3cR, or 4R via the post-analysis rack holding section 34 or post-process rack holding section 44, and then transported rightward by the return line to be finally collected by the sample feed and collection device 2. The structure of the sample processing apparatus 1 is described in detail below.

Figure 2:
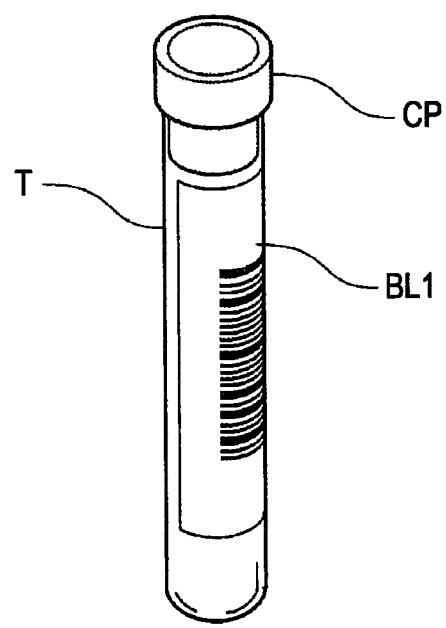
FIG. 2 is a perspective view illustrating an outer appearance of a sample container.
Figure 3:
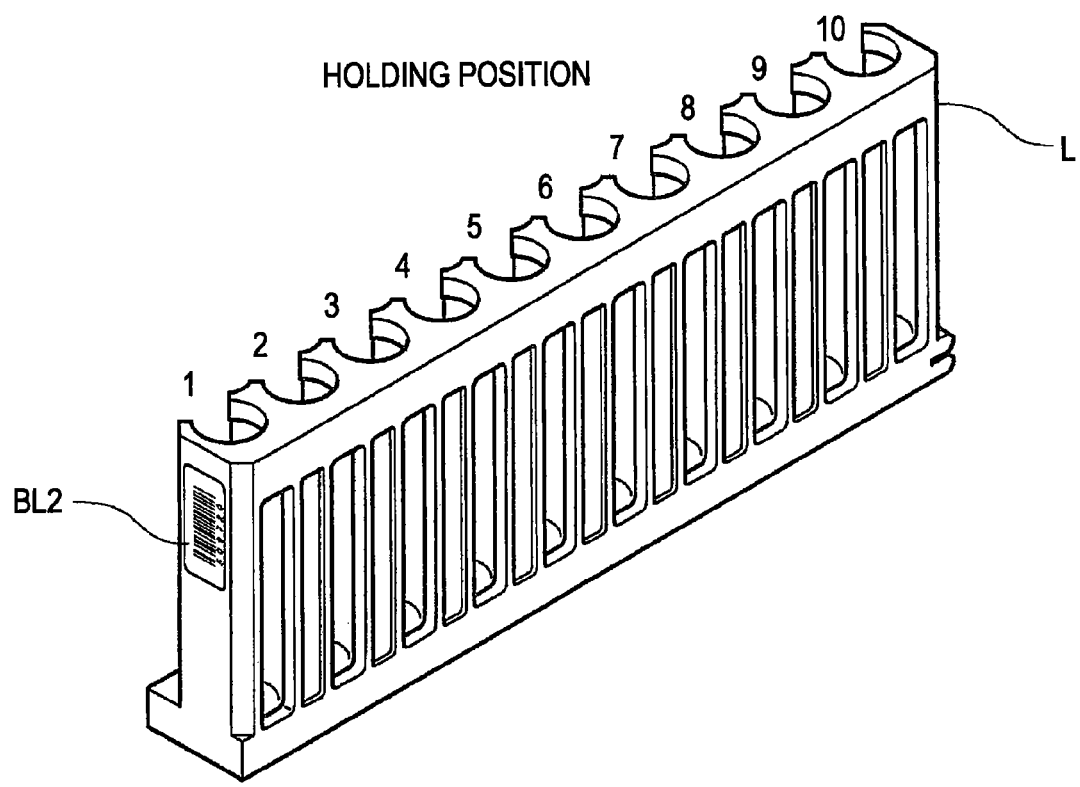
FIG. 3 is a perspective view illustrating an outer appearance of a sample rack.

FIG. 2 is a perspective view illustrating an outer appearance of a sample container, and FIG. 3 is a perspective view illustrating an outer appearance of a sample rack. As illustrated in FIG. 2, a sample container T is formed in a tubular shape having an open upper end. The sample container contains therein blood collected from a patient as a sample, and its upper-end opening is sealed with a cap portion CP. The sample container T is made of optically transparent glass or synthetic resin so that the blood sample inside is visible. A barcode label BL1 is affixed to a side surface of the sample container T. The barcode label BL1 has a barcode (sample barcode) representing a sample ID printed thereon. The sample rack L can hold 10 sample containers T in an aligned manner. The sample rack L holds the sample containers T perpendicularly (upright position). A barcode label BL2 is affixed to a side surface of the sample rack L. The barcode label BL2 has a barcode (rack barcode) representing a rack ID printed thereon.

[Structure of Sample Feed and Collection Device 2]

As illustrated in FIG. 1, the sample feed and collection device 2 has a sample feed unit 21, a pre-processing unit 22, and a sample collection unit 23. The sample feed and collection device 2 can house therein a sample rack holding a plurality of sample containers.

The sample feed unit 21 can house therein the sample rack L placed in the apparatus by a user. The sample feed unit 21 can transfer the sample rack L set by the user to the rearmost side of the sample feed unit 21 (Y1 direction) and deliver the sample rack L to the left side of the sample feed unit 21 (to the side of the pre-processing unit 22).

The pre-processing unit 22 is connected to the left side of the sample feed unit 21 to receive the sample rack L sent out from the sample feed unit 21. The pre-processing unit 22 has a barcode reader 22b. The barcode reader 22b can read the sample ID from the barcode label BL1 of the sample container T held in the sample rack L and also read the rack ID from the rack barcode label BL2 of the sample rack L. The pre-processing unit 22 can transfer the sample rack L already barcode-read by the barcode reader 22b to the front side of the pre-processing unit 22 (Y2 direction) and thereafter transport the sample rack L to the left side of the pre-processing unit 22 (to the side of the sample transport unit 3a). In vicinity of a rack delivering position at which the rack is transported from the pre-processing unit 22 to the sample transport unit 3a, a dedicated barcode reader 222a for reading the rack barcode of the sample rack L is provided. The sample rack L sent out from the pre-processing unit 22 is guided to the transport line 3aF of the sample transport device 3. The pre-processing unit 22 has a controller 22a including a CPU, a memory, and the like. The controller 22a controls the feature of the pre-processing unit 22.

The sample collection unit 23 is provided on the right side of the sample feed unit 21 and has a structure similar to that of the sample feed unit 21. The sample collection unit 23 collects the sample rack L delivered thereinto by the return line 3aR and collection lines 223, 217, and 237.

[Structure of Sample Transport Device 3]

The structure of the sample transport device 3 is described below. As illustrated in FIG. 1, the sample processing apparatus 1 has the sample transport device 3 including the sample transport units 3a, 3b, 3c, and 4. The sample transport units 3a, 3b, and 3c are respectively provided on the front side of the measurement units 51, 52, and 53 of the hemocyte analyzing device 5. Of the sample transport units 3a, 3b, and 3c, two of the adjacent sample transport units are connected to each other so that the sample rack L can be delivered and received therebetween. The rightmost sample transport unit 3a is connected to the sample feed and collection device 2 to receive the sample rack L carried out of the sample feed and collection device 2 and send the sample rack L back to the sample feed and collection device 2.

Figure 4:
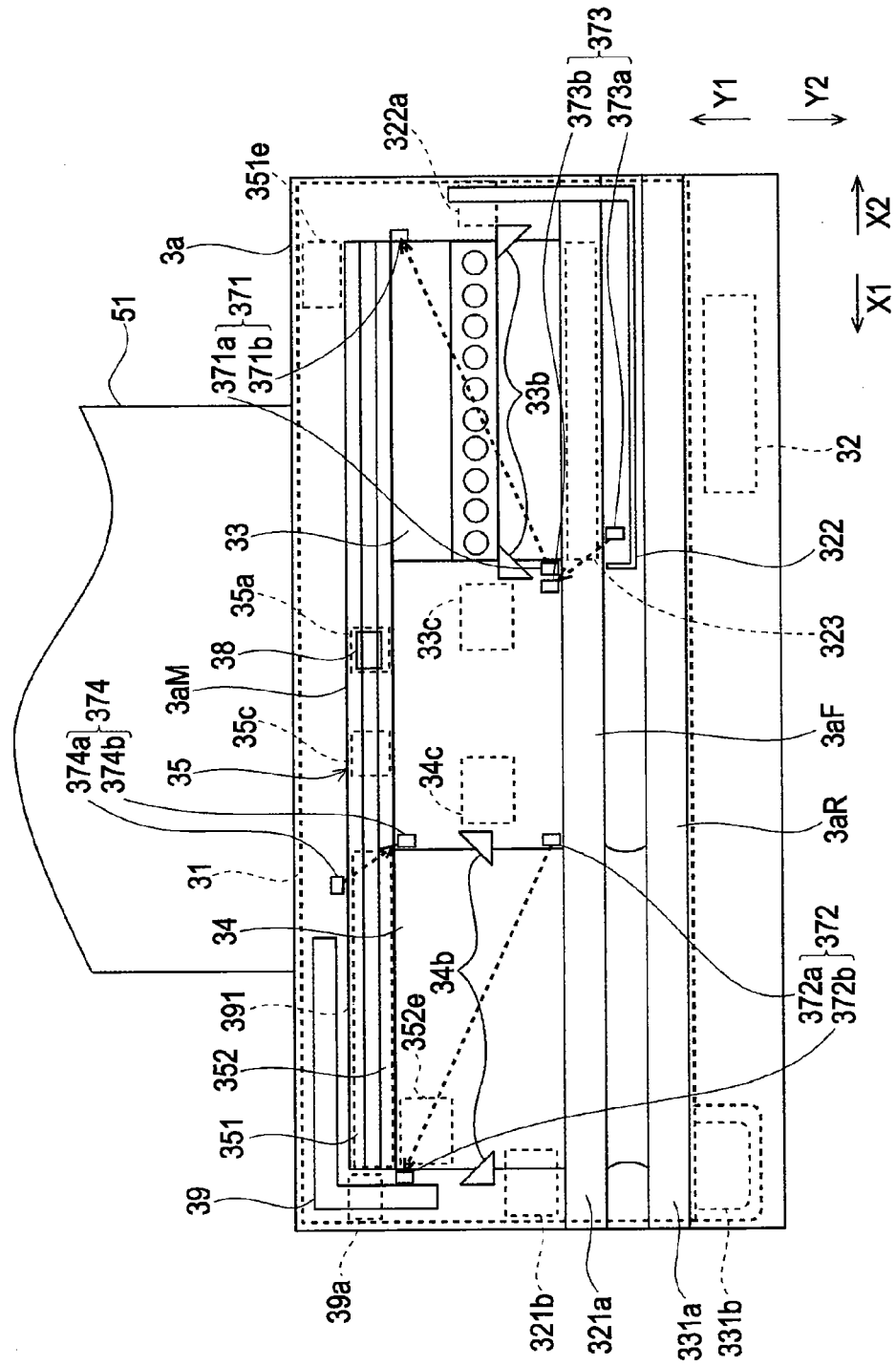
FIG. 4 is a plan view illustrating a structure of a sample transport unit used in a hemocyte analyzing device according to the embodiment.

FIG. 4 is a plan view illustrating the structure of the sample transport unit 3a. In this section, the sample transport unit 3a on the front side of the measurement unit 51 is described. The description given below is also applied to the structures of the other sample transport units 3b and 3c disposed on the front side of the measurement units 52 and 53. As illustrated in FIG. 4, the sample transport unit 3a has a transport mechanism 31 which transports the sample, and a controller 32 which controls the transport mechanism 31. The transport mechanism 31 has a pre-analysis rack holding section 33, a post-analysis rack holding section 34, a measurement line 3aM (first transport path) which horizontally transfers the sample rack L in the direction of arrow X in the drawing and transports the sample rack L received from the pre-analysis rack holding section 33 to the post-analysis rack holding section 34 so that the sample is supplied to the measurement unit 51, a transport line 3aF (second transport path) which accepts the sample rack L from the device on the transport upstream side (sample feed and collection device 2) and transports the sample rack L to the device on the transport downstream side (sample transport unit 3b) without supplying the sample contained in the sample rack L to the measurement unit 51, and a return line 3aR (third transport path) which accepts the sample rack L from the device on the transport downstream side (sample transport unit 3b) and transports the sample rack L to the device on the transport upstream side (sample feed and collection device 2) without supplying the sample contained in the sample rack L to the measurement unit 51.

The transport line 3aF has an annular belt 321a and a stepping motor 321b. The transport line 3aF can rotate the belt 321a in the direction of arrow X1 using a driving force of the stepping motor 321b to thereby transfer the sample rack L disposed on the belt 321a in the direction of arrow X1. The sample rack L can be transported by the transport lines 3aF, 3bF, and 3cF of the sample transport units 3a, 3b, and 3c, and a transport line 4F of the sample transport unit 4 which will be described later.

At positions away from the transport line 3aF by a predetermined distance in the forward direction, the return line 3aR in parallel with the transport line 3aF is provided. The return line 3aR has an annular belt 331a and a stepping motor 331b. The return line 3aR can rotate the belt 331a in the direction of arrow X2 using a driving force of the stepping motor 331b to thereby transfer the sample rack L disposed on the belt 331a in the direction of arrow X2. The sample rack L can be transported by the return lines 3aR, 3bR, and 3cR of the sample transport units 3a, 3b, and 3c, and the return line 4R of the sample transport unit 4 which will be described later.

On the front side of the pre-analysis rack holding section 33, a rack delivering portion 322 is provided between the transport line 3aF and the return line 3aR so as to face the pre-analysis rack holding section 33. The rack delivering portion 322 is horizontally transferred in a linear manner in the direction of arrow Y1 (rearward) by a driving force of the stepping motor 322a. Accordingly, when the sample rack L is transported by the transport line 3aF from the device on the transport upstream side to finally arrive at a position 323 on the transport line 3aF between the pre-analysis rack holding section 33 and the rack delivering portion 322 (hereinafter, called a "pre-analysis rack delivering position"), the rack delivering portion 322 is transferred to the side of the pre-analysis rack holding section 33 to push the sample rack L into the pre-analysis rack holding section 33. The sample transport unit 3a is equipped with a rack sensor 373 which detects the sample rack L that arrived at the pre-analysis rack delivering position 323. The rack sensor 373 has a photoemitter 373a and a photoreceiver 373b.

The pre-analysis rack holding section 33 has a rectangular shape in planar view. The lateral length of the pre-analysis rack holding section 33 is slightly larger than that of the sample rack L, and its width (length in front-back direction) is slightly larger than twice the width of the sample rack L. The pre-analysis rack holding section 33 is formed in a height lower than any other surface around it, and the pre-analysis sample rack L is disposed on an upper surface thereof. In other words, the pre-analysis rack holding section 33 can hold two sample racks L at a time. The pre-analysis rack holding section 33 is continuous from the transport line 3aF so that the sample rack L is delivered thereinto from the transport line 3aF by the rack delivering portion 322. In vicinity of the pre-analysis rack holding section 33, a rack sensor 371 is mounted, and the sample rack L placed in the pre-analysis rack holding section 33 is detected by the rack sensor 371. The rack sensor 371 is an optical sensor, having a photoemitter 371a and a photoreceiver 371b. The photoemitter 371a is provided on a lateral side of the pre-analysis rack holding section 33, while the photoreceiver 371b is provided on a straight line which traverses the pre-analysis rack holding section 33 slantwise toward its front side from the photoemitter 371a. The photoemitter 371a is positioned so that light is emitted diagonally forward, and the photoreceiver 371b is positioned to be able to receive the emitted light. Therefore, the sample rack L transported from the transport line 3aF is placed in the pre-analysis rack holding section 33, and the sample rack L thus placed blocks the light emitted from the photoemitter 371a to lower the light reception of the photoreceiver 371b. As a result, the sample rack L can be detected by the rack sensor 371. Rack senders 33b protrude inward from the both surfaces of the pre-analysis rack holding section 33. When the sample rack L is detected by the rack sensor 371, the rack senders 33b shift rearward (direction toward the measurement line 3aM) to be engaged with the sample rack L, and thereby transport the sample rack L rearward. The rack senders 33b can be driven by a stepping motor 33c provided below the pre-analysis rack holding section 33.

On the transport path where the sample rack L is transported by the measurement line 3aM, there are a sample container detecting position 35a at which the sample container is detected by a sample container sensor 38, and a sample feeding position 35c at which the sample is fed to the measurement unit 51 of the hemocyte analyzing device 5. The measurement line 3aM can transport the sample rack L so that the sample is transported to the sample feeding position 35c via the sample container detecting position 35a. The sample feeding position 35c is a position provided on the transport downstream side away from the sample container detecting position 35a by a dimension equal to one sample. When the sample is transported to the sample feeding position 35c by the measurement line 3aM, a hand portion of the measurement unit 51 of the hemocyte analyzing device 5, which will be described later, grips the sample container T containing therein the sample to take the sample container T out of the sample rack L, and suctions the sample from the sample container T. As a result, the sample is supplied to the measurement unit 51. After the sample container is transported to the sample feeding position 35c, the measurement line 3aM is on standby to transport the sample rack L until the sample container T is returned to the sample rack L after the sample is supplied.

The measurement line 3aM has a first belt 351 and a second belt 352 which independently operate, and a stepping motor 351e which drives the first belt 351 and a stepping motor 352e which drives the second belt 352.

A rack delivering section 39, which will be described later, is provided so as to face the post-analysis rack holding section 34 with the measurement line 3aM interposed therebetween. The rack delivering section 39 horizontally travels in the direction of arrow Y in a linear manner by a driving force of a stepping motor 39a. Accordingly, when the sample rack L is transported to a position 391 between the post-analysis rack holding section 34 and the rack delivering section 39 (hereinafter, called a "post-analysis rack delivering position"), the rack delivering section 39 is moved to the side of the post-analysis rack holding section 34 to push the sample rack L into the post-analysis rack holding section 34. As described above, the analysis-completed sample rack L is transported from the measurement line 3aM to the post-analysis rack holding section 34. The sample transport unit 3a is provided with a rack sensor 374 which detects the sample rack which arrived at the post-analysis rack delivering position 391. The rack sensor 374 has a photoemitter 374a and a photoreceiver 374b.

The post-analysis rack holding section 34 has a rectangular shape in planar view. The lateral length of the post-analysis rack holding section 34 is slightly larger than that of the sample rack L, and its width (length in front-back direction) is slightly larger than twice the width of the sample rack L. The post-analysis rack holding section 34 is formed in a height lower than any other surface around it, and the analysis-completed sample rack L is disposed on an upper surface thereof. In other words, the post-analysis rack holding section 34 can hold two sample racks L at a time. The post-analysis rack holding section 34 is continuous from the measurement line 3aM so that the sample rack L is delivered thereinto from the measurement line 3aM by the rack delivering section 39 as described above. In vicinity of the post-analysis rack holding section 34, a rack sensor 372 is mounted, and the sample rack L placed in the post-analysis rack holding section 34 is detected by the rack sensor 372. The rack sensor 372 is an optical sensor, having a photoemitter 372a and a photoreceiver 372b. The photoemitter 372a is provided on a lateral side of the post-analysis rack holding section 34, while the photoreceiver 372b is provided on a straight line which traverses the post-analysis rack holding section 34 slantwise toward its front side from the photoemitter 372a. The photoemitter 372a is positioned so that light is emitted diagonally forward, and the photoreceiver 372b is positioned to be able to receive the emitted light. Therefore, the sample rack L transported from the rack delivering section 39 is placed in the post-analysis rack holding section 34, and the sample rack L thus placed blocks the light emitted from the photoemitter 372a to lower the light reception of the photoreceiver 372b. As a result, the sample rack L can be detected by the rack sensor 372. Rack senders 34b protrude inward from the both surfaces of the post-analysis rack holding section 34. When the sample rack L is detected by the rack sensor 372, the rack senders 34b shift forward (direction toward the transport line 3aF and return line 3aR) to be engaged with the sample rack L, and thereby transport the sample rack L forward. The rack senders 34b can be driven by a stepping motor 34c provided below the post-analysis rack holding section 34. Further, the post-analysis rack holding section 34 is continuous from the transport line 3aF and the return line 3aR. According to the structure, the rack senders 34b can transport the sample rack L placed in the post-analysis rack holding section 34 to one of the transport line 3aF and the return line 3aR.

The transport mechanism 31 having above structure is mostly controlled by the controller 32. The controller 32 includes a CPU, a ROM, a RAM, and the like (not illustrated). The controller 32 can run a control program of the transport mechanism 31 stored in the ROM on the CPU. The controller 32 is equipped with an Ethernet (registered trademark) interface and connected to the information processing unit 54 and the system control device 8 via LAN to allow communication therebetween.

Of the structural elements of the transport mechanism 31, the rack senders 33b, measurement line 3aM, and rack delivering section 39 are controlled by the information processing unit 54 of the hemocyte analyzing device 5. The other structural elements of the transport mechanism 31 are controlled by the controller 32.

According to the structure thus far described, the sample transport unit 3a (3b, 3c) can transport the sample rack L transported from the sample feed and collection device 2 to the pre-analysis rack delivering position 323 using the transport line 3aF, transport the sample rack L to the pre-analysis rack holding section 33 using the rack delivering portion 322, and then transfer the sample rack L from the pre-analysis rack holding section 33 to the measurement line 3aM and further transport the sample rack L on the measurement line 3aM to finally supply the sample to the relevant measurement unit 51 (52, 53) of the hemocyte analyzing device 5. The sample rack L holding the suctioned sample is transported to the post-analysis rack delivering position 391 by the measurement line 3aM, and then transported to the post-analysis rack holding section 34 by the rack delivering section 39. The sample rack L held by the post-analysis rack holding section 34 is transported to the return line 3aR, and then transported to the device (sample feed and collection device 2) in the previous stage (transport upstream side) by the return line 3aR. When the sample rack L holding the sample to be processed by the measurement unit 52 or 53 on the transport downstream side or the smear preparation device 6 is received from the device in the previous stage by the sample transport unit 3, the received sample rack L is transported by the transport line 3aF in the direction of arrow X1 to be directly transported to the sample transport unit 3b in the subsequent stage. When the sample rack L collected by the sample feed and collection device 2 is received from the sample transport unit 3b in the subsequent stage by the sample transport unit 3a, the received sample rack L is transported by the return line 3aR of the sample transport unit 3a in the direction of arrow X2 to be directly transported to the sample feed and collection device 2 in the previous stage.

As illustrated in FIG. 1, the sample transport unit 4 is disposed on the front side of the smear preparation device 6. Of the three sample transport units 3a, 3b, and 3c, the sample transport unit 3c at the farthest end of the transport downstream side (left side in the drawing) is connected to the right end of the sample transport unit 4.

Figure 5:
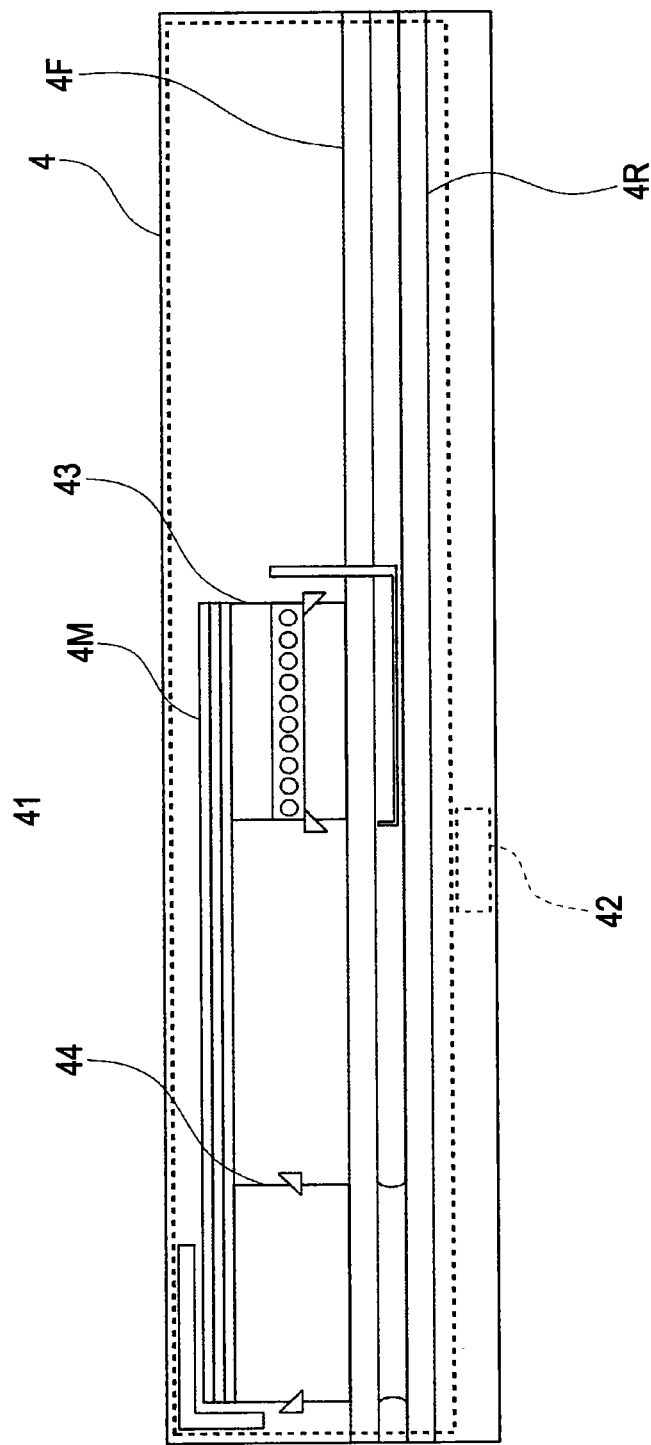
FIG. 5 is a plan view illustrating a structure of a sample transport unit used in a smear preparation device according to the embodiment.

FIG. 5 is a plan view illustrating the structure of the sample transport unit 4. The sample transport unit 4 has a transport mechanism 41 which transports a sample, and a controller 42 which controls the transport mechanism 41. The transport mechanism 41 has a pre-process rack holding section 43 capable of temporarily holding the sample rack L which holds the sample container T containing therein the sample from which a smear is not yet prepared, a post-process rack holding section 44 capable of temporarily holding the sample rack L which holds the sample container T from which the sample has been suctioned by the smear preparation device 6, a processing line 4M which horizontally moves the sample rack L in a linear manner in the direction of X1 and transports the sample rack L received from the pre-process rack holding section 43 to the post-process rack holding section 44 so that the sample is supplied to the smear preparation device 6, a transport line 4F which accepts the sample rack L from the sample transport unit 3c on the transport upstream side and transports the sample rack L in the direction of X1, and a return line 4R which transports the sample rack L to the sample transport unit 3c on the transport upstream side so that the sample rack L in which the smear preparation is completed is collected by the sample feed and collection device 2. The structural elements of the sample transport device 4 have dimensions, shapes and positions different to those of the sample transport units 3a, 3b, and 3c. However, they are functionally similar to the sample transport units 3a, 3b, and 3c. Therefore, description of these structural elements is omitted.

The sample transport unit 4 accepts the sample rack L transported from the sample transport unit 3c on the upstream side using the transport line 4F, transports the sample rack L to the pre-process rack holding section 43 using a rack delivering section not illustrated, and then transfers the sample rack L from the pre-process rack holding section 43 to the processing line 4M so that the sample rack L is transported by the processing line 4M. As a result, the sample can be supplied to the smear preparation device 6. The sample rack L holding the suctioned sample is transported on the processing line 4M to the post-process rack holding section 44 by a rack delivering section not illustrated. The sample rack L held by the post-process rack holding section 44 is transferred to the return line 4R, and transported by the return line 4R to the sample transport unit 3c in the previous stage (transport upstream side).

<Structure of Hemocyte Analyzing Device 5>

The hemocyte analyzing device 5 is a multiple hemocyte analyzing device which uses optical flow cytometry. A side scattered light intensity and a fluorescence intensity, for example, of hemocytes included in blood collected as a sample are obtained to classify types of the hemocytes included in the sample based on the obtained intensities. Further, the hemocytes of the different types are separately counted, and a scattergram in which the hemocytes thus classified are shown in different colors is created and displayed. The hemocyte analyzing device 5 has measurement units 51, 52, and 53 which measure blood collected as a sample, and an information processing unit 54 which processes measured data outputted from the measurement units 51, 52, and 53 and displays an analysis result of the blood sample.

As illustrated in FIG. 1, the hemocyte analyzing device 5 has three measurement units 51, 52, and 53 and one information processing unit 54. The information processing unit 54 is connected to the three measurement units 51, 52, and 53 to allow communication therebetween. The information processing unit 54 can control the operations of the three measurement units 51, 52, and 53. The information processing unit 54 is also connected to the three sample transport units 3a, 3b, and 3c disposed on the front side of the three measurement units 51, 52, and 53.

Figure 6:
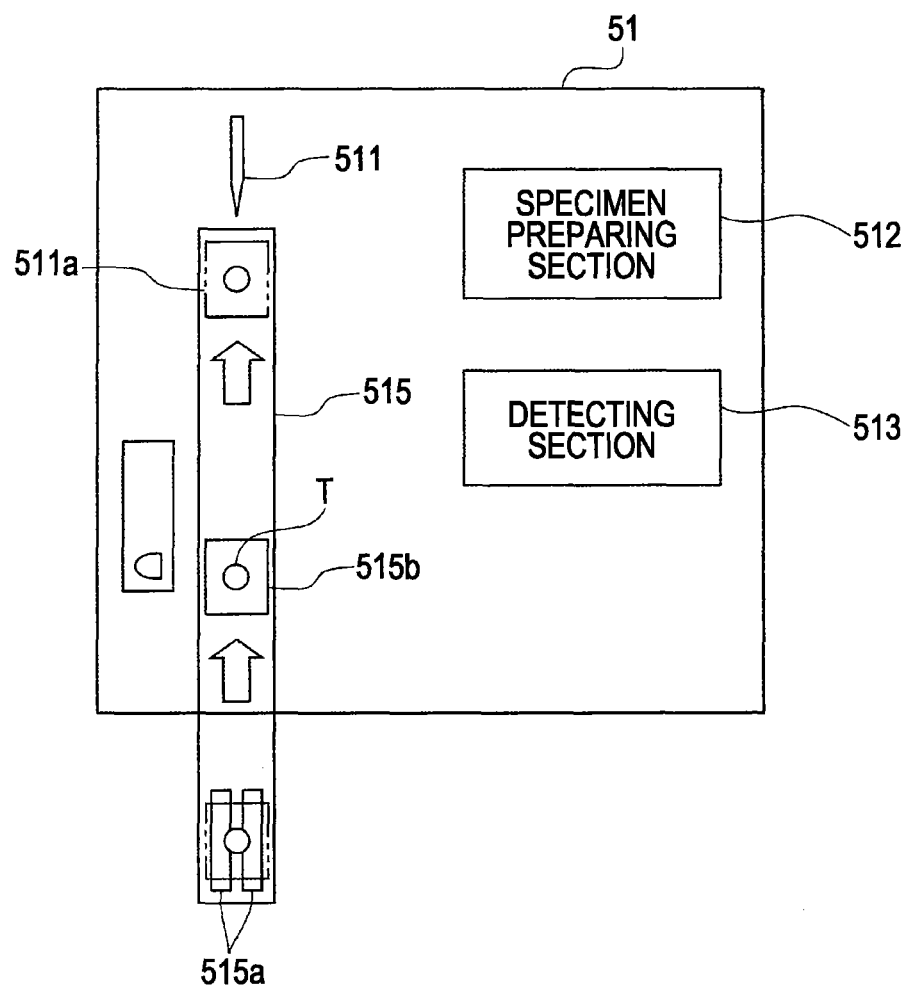
FIG. 6 is a block diagram illustrating a structure of a measurement unit provided in the hemocyte analyzing device according to the embodiment.

FIG. 6 is a block diagram illustrating the structure of the measurement unit 51. As illustrated in FIG. 6, the measurement unit 51 has a sample suctioning section 511 which suctions the blood sample from the sample container (blood collection tube) T, a specimen preparing section 512 which prepares a measurement specimen from the blood suctioned by the sample suctioning section 511, and a detecting section 513 which detects hemocytes from the measurement specimen prepared by the specimen preparing section 512. The measurement unit 51 further has a fetching port (not illustrated) through which the sample container T held in the sample rack L transported by the measurement line 3aM of the sample transport unit 3a is fetched inside, and a sample container transport section 515 which fetches the sample container T into the measurement unit 51 from the sample rack L and transports the fetched sample container T to a suctioning position where the sample is suctioned by the sample suctioning section 511.

The detecting section 513 is able to detect RBC (red blood cells) and PLT (platelets) by employing sheath flow DC detection. The detecting section 513 is able to detect HGB (hemoglobin) by employing SLS-hemoglobin method and detect WBC (white blood cells) by employing flow cytometry in which a semiconductor laser is used. The RBC, PLT, HGB, WBC are measured when CBC (complete blood count) is determined.

The sample container transport section 515 has a hand portion 515a which can grip the sample container T. The sample container transport section 515 can move the hand portion 515a upward and downward, and also forward and backward (Y direction). The hand portion 515a takes the sample container T at the feeding position 35c out of the sample rack L and sets the sample container T in a recess of a sample container setter 515b. The sample container setter 515b is then moved to the suctioning position.

Similarly to the measurement unit 51, the measurement units 52 and 53 each has a sample suctioning section, a specimen preparing section, a detecting section, and a sample container transport section. Unlike the detecting section 513 of the measurement unit 51, however, the detecting section of the measurement unit 52 can divide the white blood cells into five types (DIFF) in addition to CBC. More specifically, the detecting section of the measurement unit 52 can detect WBC (white blood cell), NEUT (neutrophile), LYMPH (lymphocyte), EO (eosinocyte), BASO (basocyte), and MONO (monocyte) by employing flow cytometry in which a semiconductor laser is used.

Unlike the detecting sections of the measurement units 51 and 52, the detecting section of the measurement unit 53 can measure reticulocyte (RET) in addition to CBC and DIFF. To measure the RET, a measurement specimen is prepared by mixing the sample with a reagent for RET measurement, and the prepared specimen is supplied to an optical detector of the detecting section for detecting WBC/DIFF (five types of WBC).

Figure 7:
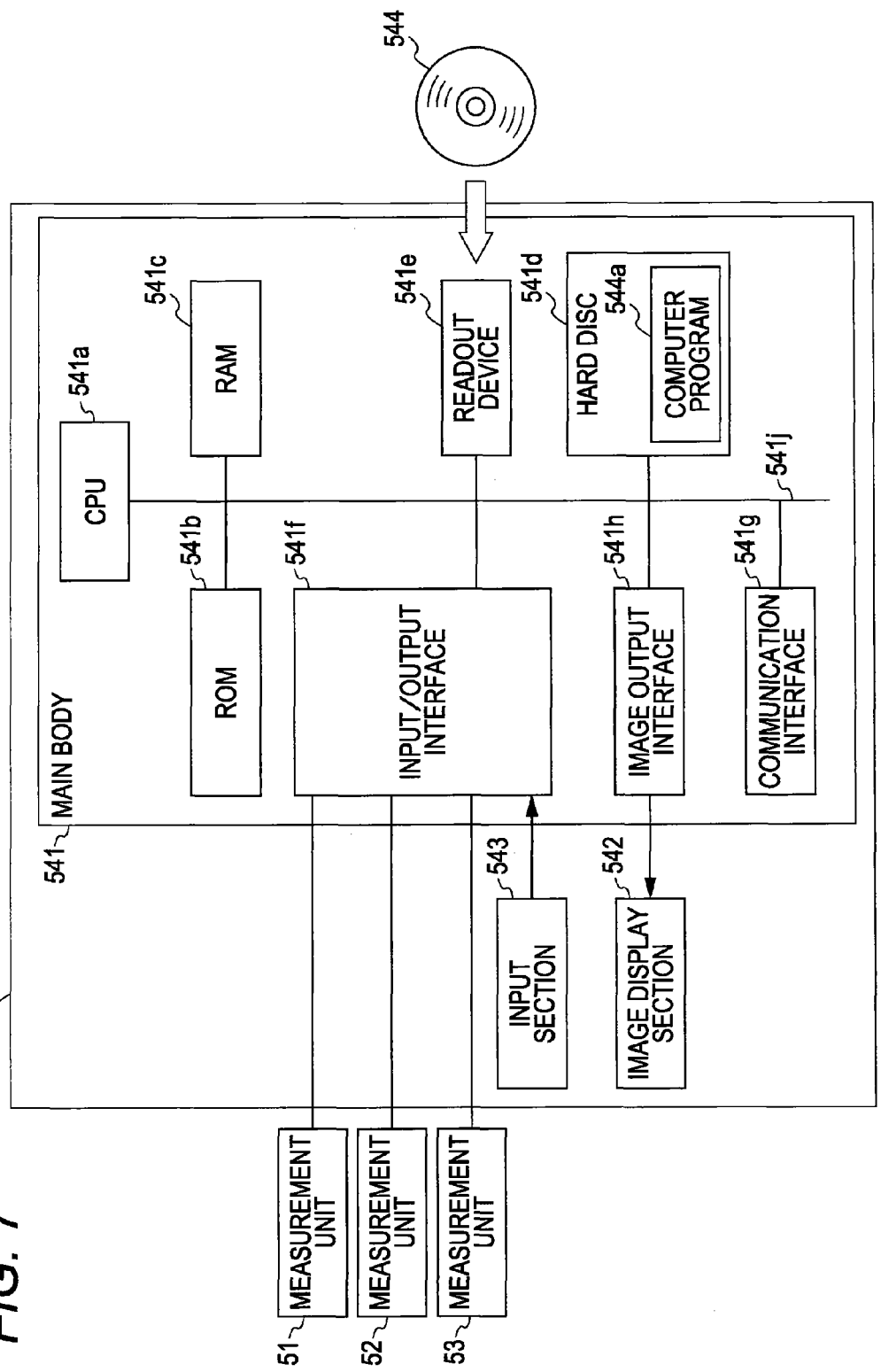
FIG. 7 is a block diagram illustrating a structure of an information processing unit provided in the hemocyte analyzing device according to the embodiment.

Hereinafter, the structure of the information processing unit 54 is described. The information processing unit 54 includes a computer. FIG. 7 is a block diagram illustrating the structure of the information processing unit 54. The information processing unit 54 is run by a computer 54a. As illustrated in FIG. 7, the computer 54a has a main body 541, an image display section 542, and an input section 543. The main body 541 has a CPU 541a, a ROM 541b, a RAM 541c, a hard disc 541d, a readout device 541e, an input/output interface 541f, a communication interface 541g, and an image output interface 541h. The CPU 541a, the ROM 541b, the RAM 541c, the hard disc 541d, the readout device 541e, the input/output interface 541f, the communication interface 541g, and the image output interface 541h are connected to one another by a bus 541j.

The readout device 541e can read a computer program 544a which makes the computer function as the information processing unit 54 from a transportable recording medium 544, and install the read computer program 544a in the hard disc 541d.

<Structure of Smear Preparation Device 6>

To produce a smear, the smear preparation device 6 suctions the blood sample and drops the suctioned blood on a glass side, spreads the dropped sample on the glass slide very thin, and supplies a staining liquid on the glass slide to stain the blood thereon after drying the sample.

Figure 8:
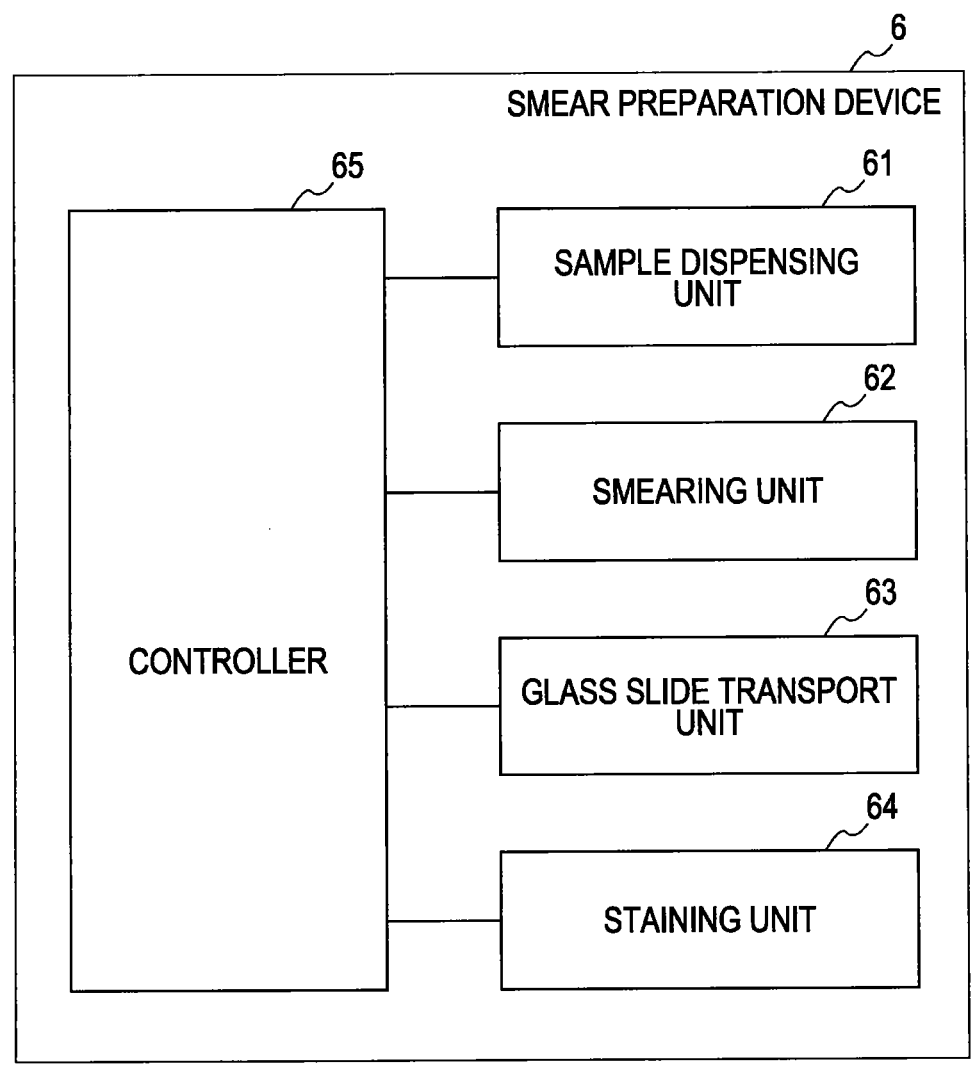
FIG. 8 is a block diagram illustrating a schematic structure of the smear preparation device according to the embodiment.

FIG. 8 is a block diagram illustrating the schematic structure of the smear preparation device 6. As illustrated in FIG. 8, the smear preparation device 6 has a sample dispensing unit 61, a smearing unit 62, a glass slide transport unit 63, a staining unit 64, and a controller 65.

The sample dispensing unit 61 has a suctioning tube (not illustrated). The sample dispensing unit 61 penetrates the suctioning tube into the cap portion CP of the sample container T held in the sample rack L transported on the processing line 4M of the sample transport unit 4 to suction the blood sample from the sample container T. The sample dispensing unit 61 drops the suctioned blood sample on the glass slide. The smearing unit 62 smears the blood sample dropped on the glass side, and dries and prints the dropped blood sample on the glass slide.

The glass slide transport unit 63 is provided to house the glass slide on which the blood sample is smeared by the smearing unit 62 in a cassette not illustrated and transport the cassette. The staining unit 64 supplies the staining solution to the glass slide in the cassette transported to a staining position by the glass slide transport unit 63. The controller 65 controls the sample dispensing unit 61, smearing unit 62, glass slide transport unit 63, and staining unit 64 in accordance with a sample preparation instruction obtained from the sample transport device 3 to carry out the smear preparing operation described earlier.

<Structure of System Control Device 8>

The system control device 8 including a computer controls the overall operation of the sample processing device 1. The system control device 8 receives a number affixed to the sample rack L from the sample feed and collection device 2 and decides a destination of the sample rack L, and then transmits transport instruction data indicating the decided destination to the sample transport device 3.

Figure 9:
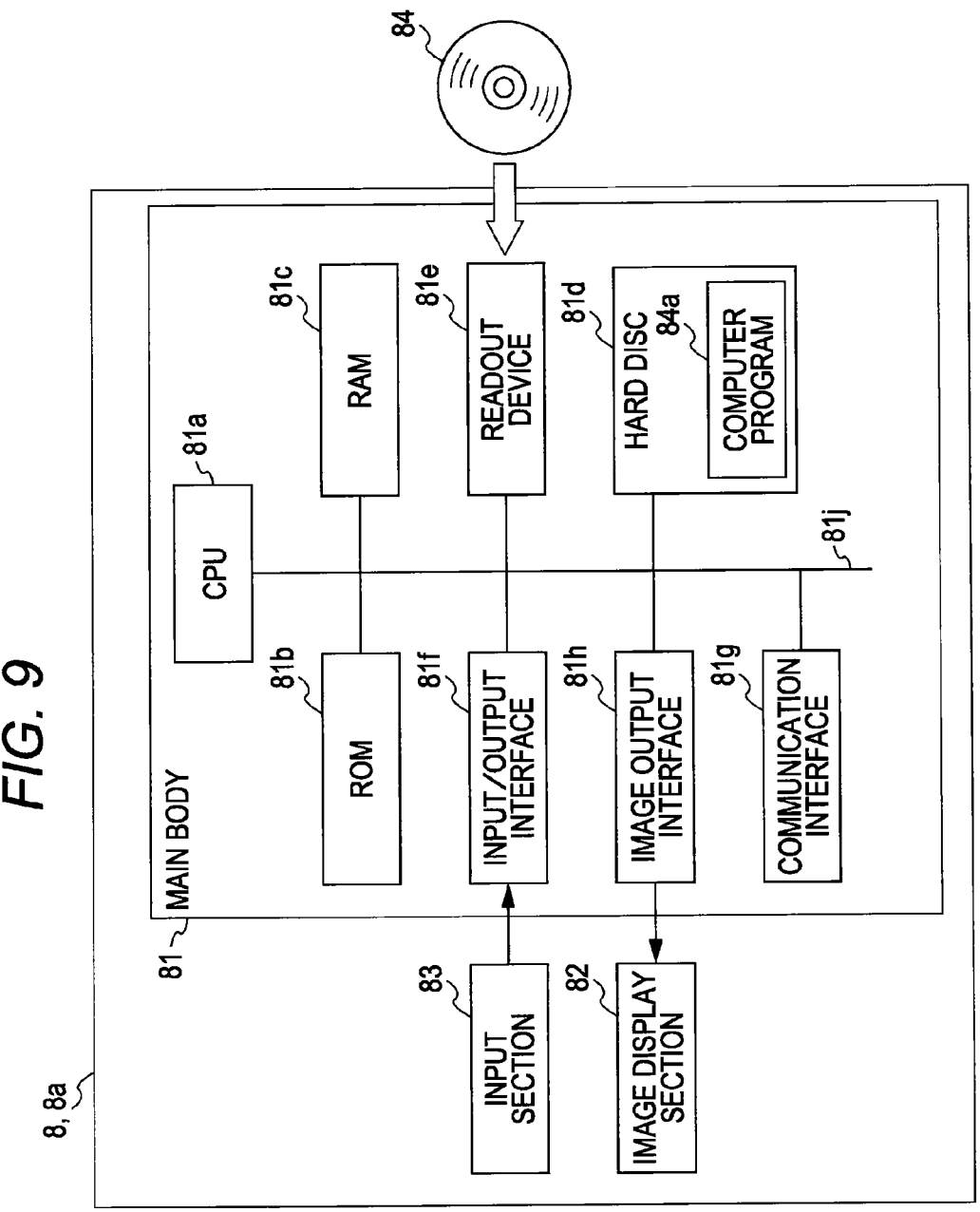
FIG. 9 is a block diagram illustrating a structure of a system control device according to the embodiment.

FIG. 9 is a block diagram illustrating the structure of the system control device 8. The system control device 8 is run by a computer 8a. As illustrated in FIG. 9, the computer 8a has a main body 81, an image display section 82, and an input section 83. The main body 81 has a CPU 81a, a ROM 81b, a RAM 81c, a hard disc 81d, a readout device 81e, an input/output interface 81f, a communication interface 81g, and an image output interface 81h. The CPU 81a, the ROM 81b, the RAM 81c, the hard disc 81d, the readout device 81e, the input/output interface 81f, the communication interface 81g, and the image output interface 81h are connected to one another by a bus 81j.

The readout device 81e can read a system control program 84a which makes the computer function as the system control device 8 from a transportable recording medium 84, and install the system control program 84a in the hard disc 81d.

<Structure of Test Information Management Device 9>

The test information management device 9 is a device which manages information relating to tests performed in a facility, generally called LIS (Laboratory Information System), which is connected not only to the hemocyte analyzing device 5 but also to a clinical sample testing device. The test information management device 9 receives a measurement order inputted by an operator or transmitted from a device such as an electronic chart system, and stores and manages the received measurement order. Further, the test information management device 9 receives an order request from the system control device 8 and transmits the requested measurement order to the system control device 8, and also receives an analysis result from the hemocyte analyzing device 5 and stores and manages the received analysis result.

The test information management device 9 including a computer has a CPU, a ROM, a RAM, a hard disc, a communication interface, and the like. The communication interface is connected to the LAN mentioned earlier and can thereby communicate with the system control device 8 and the information processing unit 54 of the hemocyte analyzing device 5. The measurement order is stored in the hard disc. The measurement order includes information such as sample ID and sample components to be measured. When the test information management device 9 receives a request for the measurement order including the sample ID from another device, the test information management device 9 reads measured data corresponding to the received sample ID from the hard disc and transmits the read data to the device which requested the data. The rest of the structure of the test information management device 9 is similar to the other computers described so far, and will not be any further described.

Next is described a flow of the sample rack transport operation by the sample transport unit 3a, 3b, 3c of the sample transport device 3. Below is described a flow of the sample rack transport operation by the sample transport unit 3a. However, the sample transport units 3b and 3c carry out a similar sample rack transport operation. The transport operation by the sample transport unit 3a includes four transport operations, which are first and second transport operations controlled by the controller 32 of the sample transport unit 3a, and a transport operation in which the sample rack is transferred to the measurement line and a transport operation in which the sample rack is transported from the measurement line which are controlled by the information processing unit 54 of the hemocyte analyzing device 5.

<First Transport Operation by Sample Transport Unit 3a>

Figure 10:
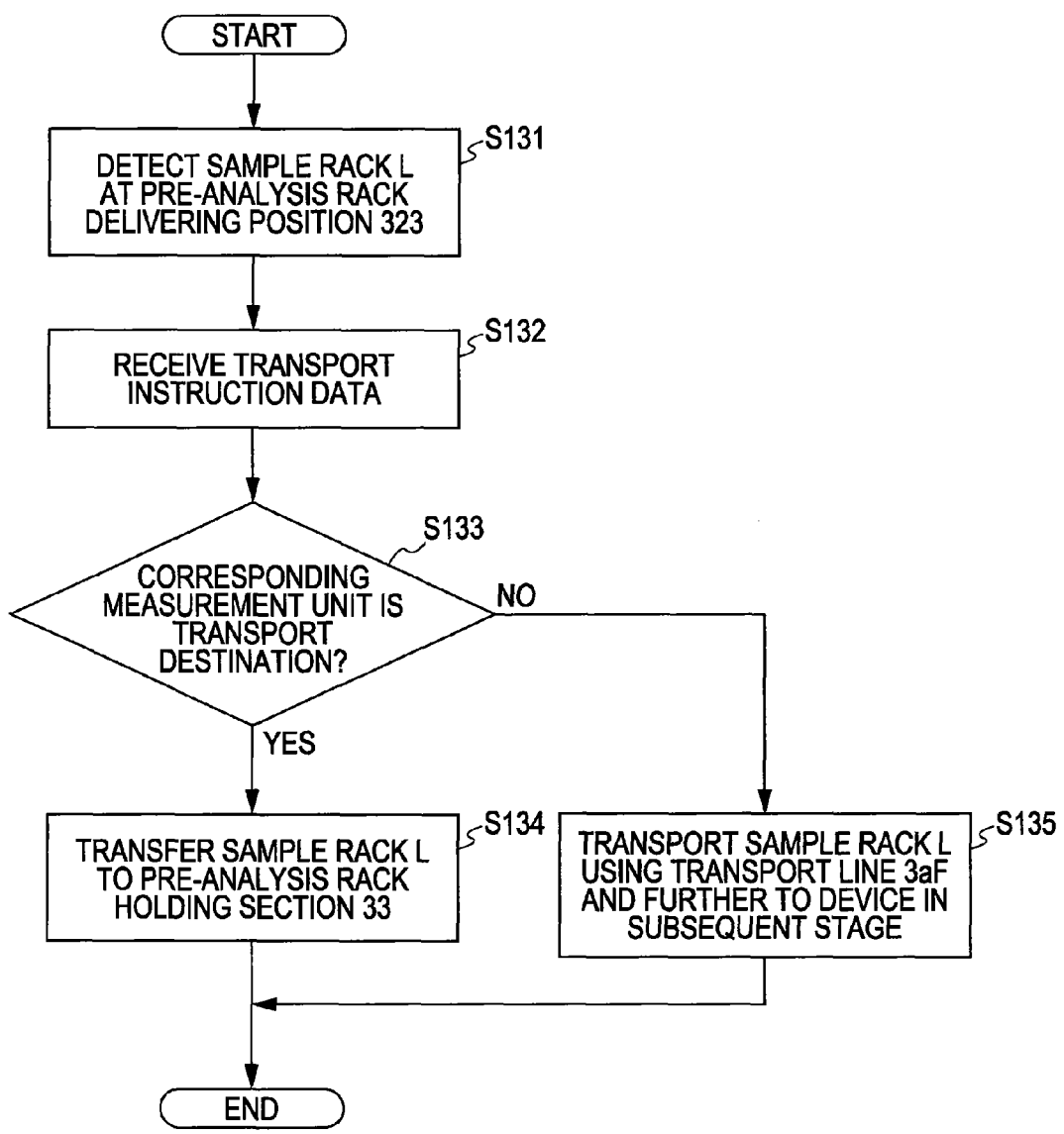
FIG. 10 is a flow chart illustrating steps of a first transport operation by the sample transport unit used in the hemocyte analyzing device according to the embodiment.

FIG. 10 is a flow chart illustrating steps of the first transport operation by the sample transport unit 3a. The controller 32 of the sample transport unit 3a carries out a processing step of S133 when the rack sensor 373 detects the sample rack L transported from the pre-processing unit 22 arrived at the pre-analysis rack delivering position 323 (step S131) and the transport instruction data of the sample rack L (data including destination of the sample rack, rack ID, holding positions of all of the samples held in the sample rack L, sample IDs, and measurement order) is received from the system control device 8 (step S132).

In step S133, the controller 32 determines whether or not the destination of the transported sample rack L is the measurement unit 51 based on the transport instruction data. In the case of the sample transport unit 3b positioned second from the transport upstream side, the controller 32 of the sample transport device 3b determines whether or not the destination of the transported sample rack L is the measurement unit 52. Having determined that the destination is the measurement unit 51 (YES in step S133), the controller 32 drives the transport mechanism 31 to transport the sample rack L using the transport line 3aF, and transports the sample rack L positioned at the pre-analysis rack delivering position 323 to the pre-analysis rack holding section 33 by moving the rack delivering portion 322 forward (step S134). The controller 32 then ends the operation.

Having determined in step 5133 that the destination is not the measurement unit 51 (NO in step S133), the controller 32 drives the transport mechanism 31 to transport the sample rack L using the transport line 3aF to directly send the sample rack to the sample transport unit 3b in the subsequent stage (step S135). Then, the controller 32 ends the operation.

<Operation for Transporting Sample Rack to Measurement Line by Hemocyte Analyzing Device 5>

Figure 11:
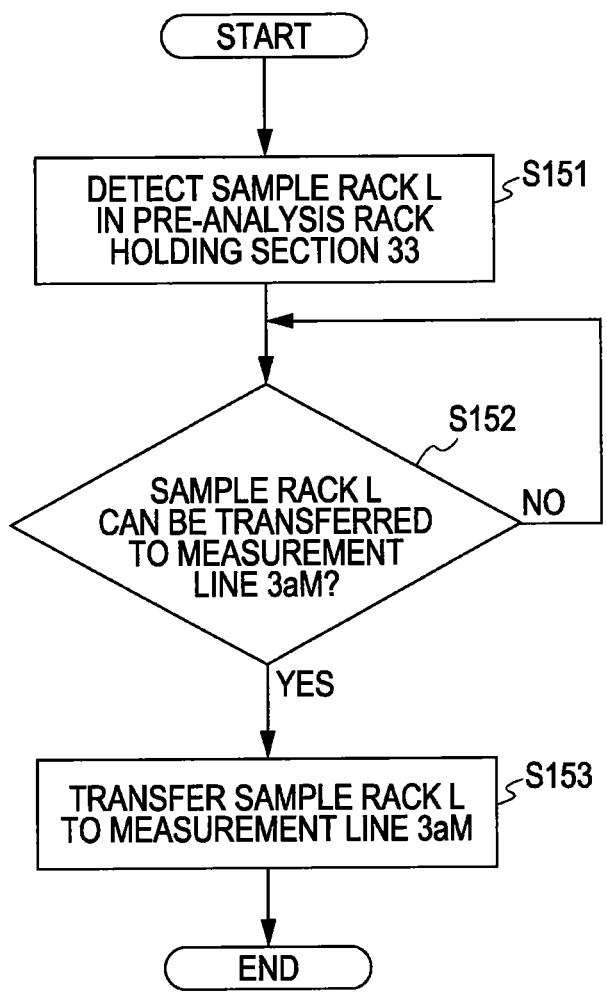
FIG. 11 is a flow chart illustrating steps of a transfer operation for transferring a sample rack to a measurement line by the hemocyte analyzing device according to the embodiment.

FIG. 11 is a flow chart illustrating steps of the operation for transporting the sample rack to the measurement line by the hemocyte analyzing device 5. When the CPU 541a of the information processing unit 54 in the hemocyte analyzing device 5 detects the sample rack L in the pre-analysis rack holding section 33 using the rack sensor 371 provided in the sample transport unit 3a (step S151), the CPU 541a carries out a processing step of S152.

In step S152, the CPU 541a determines whether or not the sample rack L can be transferred to the measurement line 3aM in the sample transport unit 3a (step S152). The measurement line 3aM is capable of transporting at most two sample racks L. The samples contained in the sample rack L are sequentially processed (measured) from the transport downstream side (left side) toward the transport upstream side (right side). During the measurement of the samples at the positions from the farthest holding position on the transport downstream side through the sixth holding position (holding positions 1 to 6) in the sample rack L previously transferred to the measurement line 3aM, the sample transport unit 3a is not allowed to transfer the sample rack L subsequent thereto to the measurement line 3aM. However, the sample transport unit 3a can transfer the subsequent sample rack L to the measurement line 3aM during the measurement of the samples at the positions from the seventh through tenth holding positions from the transport downstream side (holding positions 7 to 10). In the processing step of S152, therefore, the CPU 541a determines whether or not the sample measured at the time is any of the samples at the holding positions 7 to 10 to thereby determine whether or not the sample rack L can be transported to the measurement line 3aM. In the processing step of S152, it is also determined whether there is any sample rack L on the measurement line 3aM. With no sample rack L currently on the measurement line 3aM, it is determined that the sample rack L can be transported to the measurement line 3aM.

Having determined that the transport of the sample rack L to the measurement line 3aM is not allowed (NO in step S152), the CPU 541a repeats the determining process of step S152 until the sample rack L can be transferred to the measurement line 3aM and stands by for the transport of the sample rack L to the measurement line 3aM until then. Having determined that the transport of the sample rack L to the measurement line 3aM is allowed (YES in step S152), the CPU 541a shifts the rack senders 33b rearward to transfer the sample rack L to the measurement line 3aM (step S153). Then, the CPU 541a ends the operation.

<Operation for Transporting Sample Rack from Measurement Line by Hemocyte Analyzing Device 5>

Figure 12:
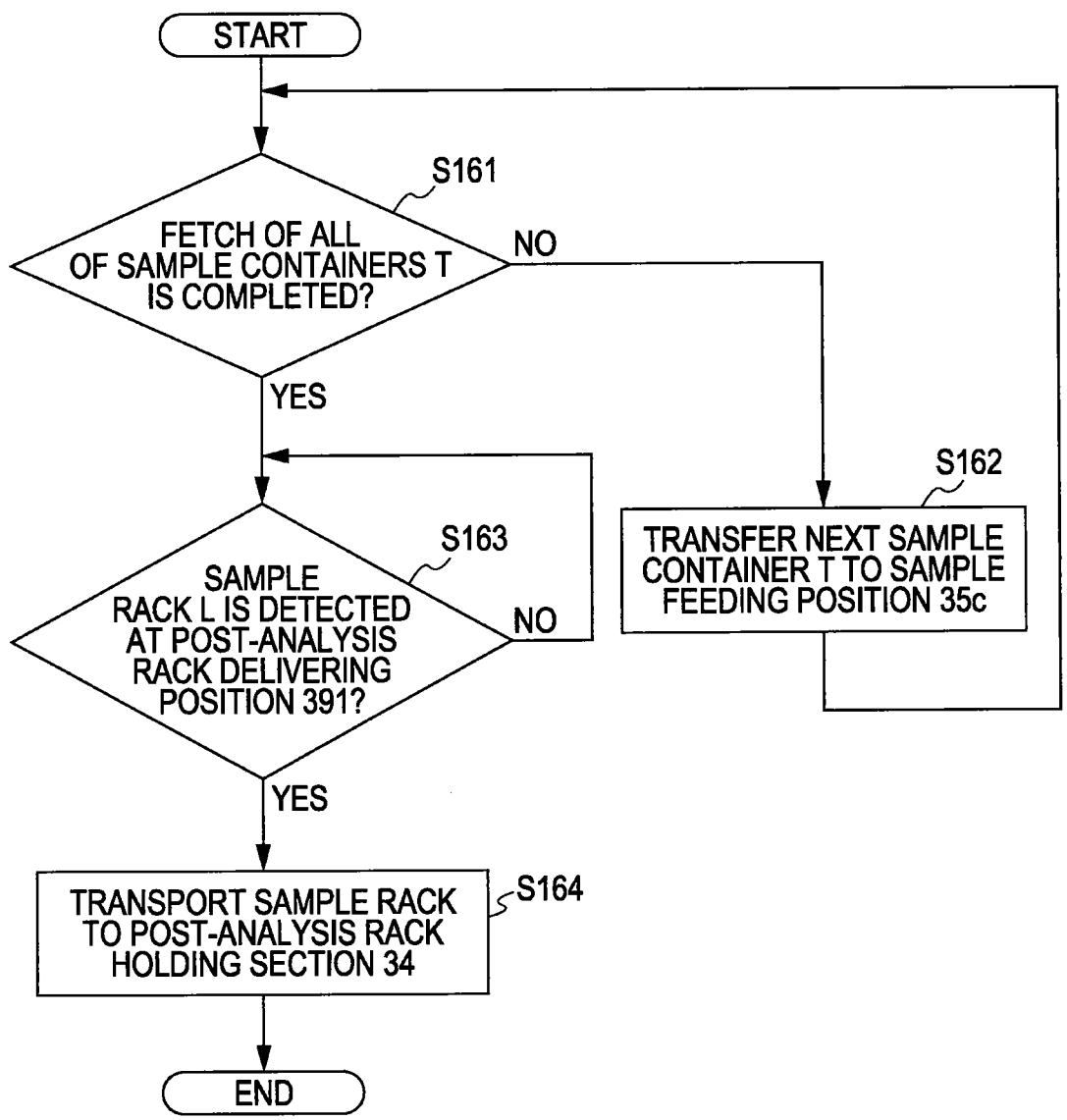
FIG. 12 is a flow chart illustrating steps of a transfer operation for transferring a sample rack from the measurement line in the hemocyte analyzing device according to the embodiment.

FIG. 12 is a flow chart illustrating steps of the operation for transferring the sample rack from the measurement line by the hemocyte analyzing device 5. In step S161, the CPU 541a determines whether or not all of the sample containers T held in the sample rack L have been fetched. Having determined that all of the sample containers T have been fetched (YES in step S161), the CPU 541a drives the measurement line 3aM to transport the sample rack L to the post-analysis rack delivering position 391. Having determined that all of the sample containers T have not been fetched, the CPU 541a transports the sample rack L so that the next sample container T is positioned at the sample feeding position 35c (step S162), and returns to the processing step of S161. When the rack sensor 374 detects the sample rack arrived at the post-analysis rack delivering position 391 (YES in step S163), the CPU 541a drives the rack delivering section 39 to transport the sample rack L to the post-analysis rack holding section 34 (step S164), and then ends the operation.

<Second Transport Operation by Sample Transport Unit 3a>

Figure 13:
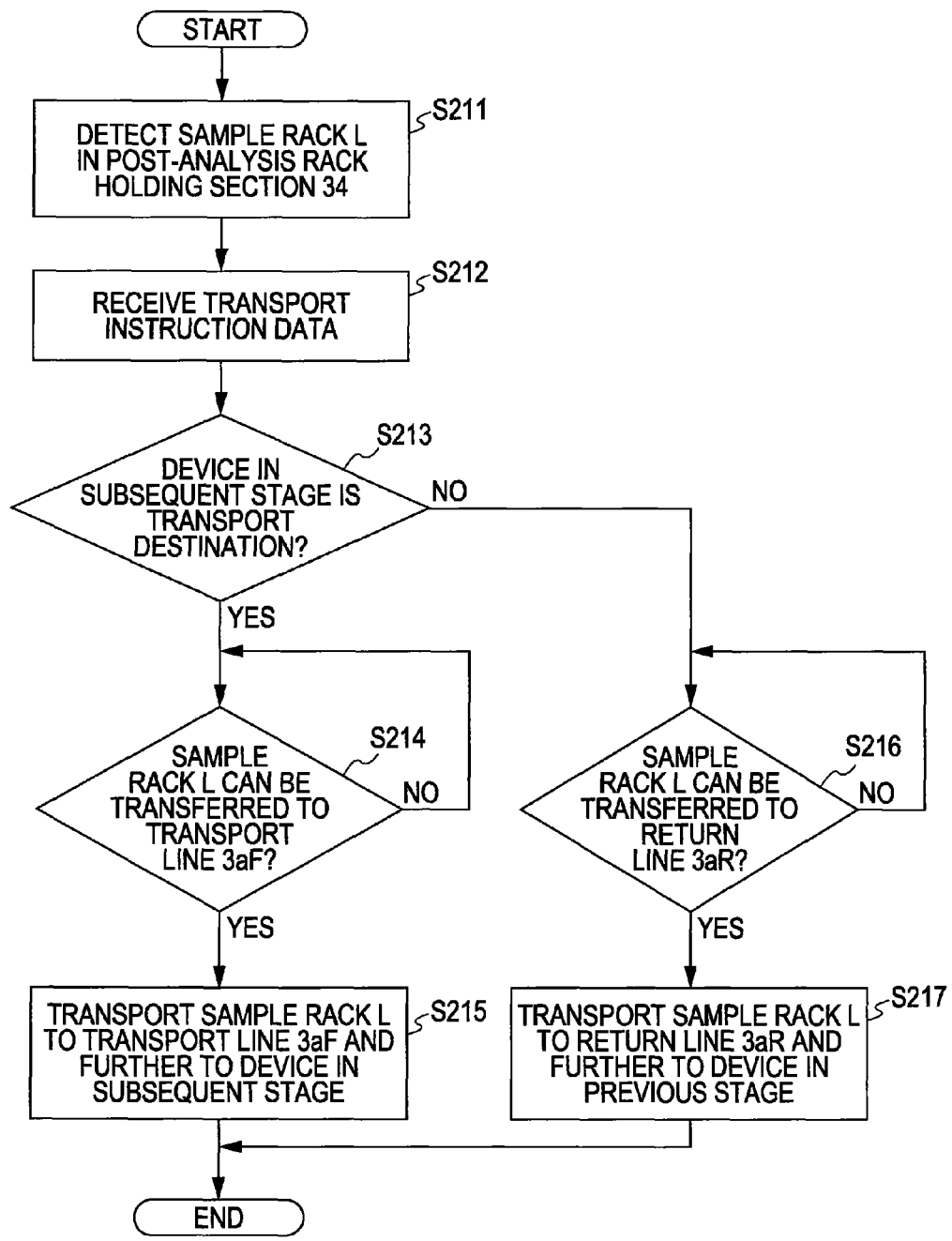
FIG. 13 is a flow chart illustrating steps of a second transport operation by the sample transport unit in the hemocyte analyzing device according to the embodiment.

FIG. 13 is a flow chart illustrating steps of the second transport operation by the controller 32 of the sample transport unit 3a. As described earlier, after the sample rack L is transported by the rack delivering section 39 of the sample transport unit 3a to the post-analysis rack holding section 34, the controller 32 detects the sample rack L using the rack sensor 372 (step S211). After the sample rack L is transported by the rack delivering section 39 of the sample transport unit 3a to the post-analysis rack holding section 34, the controller 32 receives the transport instruction data of the sample rack L (data indicating the destination of the sample rack L) from the system control device 8 (step S212). The controller 32 then determines whether or not the destination indicated by the transport instruction data is the measurement unit in the subsequent stage or the smear preparation device 6 (step S213). Having determined that the destination indicated by the transport instruction data is the measurement unit in the subsequent stage or the smear preparation device 6 (YES in step S213), the controller 32 determines whether or not the sample rack L can be transferred to the transport line 3aF (step S214). Having determined that the sample rack L can be transferred to the transport line 3aF, the controller 32 drives the transport mechanism 31 to transfer the sample rack L to the transport line 3aF using the rack senders 34b, and transport the sample rack L to the transport downstream side using the transport line 3aF (step S215). Then, the controller 32 ends the operation. Having determined that the destination indicated by the transport instruction data is neither the measurement unit in the subsequent stage nor the smear preparation device 6 (NO in step S213), the controller 32 determines whether or not the sample rack L can be transferred to the return line 3aR (step S216). Having determined that the sample rack L can be transferred to the return line 3aR, the controller 32 drives the transport mechanism 31 to transfer the sample rack L to the return line 3aR using the rack senders 34b, and transport the sample rack L to the transport upstream side using the return line 3aR (step S217). Then, the controller 32 ends the operation.

When the sample rack L is transported from the return line 3bR, 3cR, or 4R of the sample transport unit 3b, 3c, or 4 which is not on the transport upstream-most side to the sample transport unit 3a, 3b, or 3c closer to the transport upstream side than them, the controller 32 of the sample transport unit 3a, 3b, or 3c to which the sample rack L is transported drives the return line 3aR to transport the sample rack L to the transport upstream side (X2 direction) and further to the device on the upstream side (sample transport device 3a or 3b, or pre-processing unit 22).

The sample rack L transported to the pre-processing unit 22 from the return line 3aR of the sample transport unit 3a is collected by the sample collection unit 23 via the collections line 223, 217, 237.

As described so far, the sample transport unit 3a transports the sample rack L from the transport line 3aF to the measurement line 3aM by way of the pre-analysis rack holding section 33 capable of holding the sample rack L. Therefore, when the measurement unit 51 is currently measuring the samples held at the holding sections 1 to 6 of the sample rack L transported earlier, the sample rack L subsequent thereto can wait in the pre-analysis rack holding section 33. This makes it unnecessary to leave any subsequent sample rack L on hold on the transport line 3aF. Thus, there is no sample rack L retained on the transport line 3aF. As a result, the subsequent sample rack L newly introduced can be transported to the transport line 3aF. Accordingly, the subsequent sample rack L can be more smoothly transported by the transport line 3aF to the measurement unit 52 or 53 or the smear preparation device 6 on the downstream side than in the conventional apparatus. As described so far, the sample transport unit 3a transfers the sample rack L to the transport line 3aF and the return line 3aR from the measurement line 3aM via the post-analysis rack holding section 34 capable of holding the sample rack L. Therefore, in the event that the sample rack L from which all of the sample containers T have been fetched has to be temporarily transported to the post-analysis rack holding section 34 and then to the transport line 3aF from the measurement line 3aM, the sample rack L can stay in the post-analysis rack holding section 34 on standby until the transport line 3aF is ready to accept the sample rack L transported thereto. In the case where it is necessary to transport the sample rack L to the return line 3aR, the sample rack L can stay in the post-analysis rack holding section 34 on standby until the return line 3aR is ready to accept the sample rack L transported thereto. This makes it unnecessary to leave any sample rack L on hold on the measurement line 3aM. Thus, there is no sample rack L retained on the measurement line 3aM. As a result, the sample rack L can be smoothly transported on the measurement line 3aM.

The apparatus is equipped with two members separately provided, which are the rack delivering portion 322 which delivers the sample rack L at the pre-analysis rack delivering position of the transport line 3aF to the pre-analysis rack holding section 33, and the rack senders 33b which send the sample rack L held by the pre-analysis rack holding section 33 to the measurement line 3aM. According to the structure, while the rack senders 33b are sending the sample rack L held by the pre-analysis rack holding section 33 to the measurement line 3aM, the sample rack L at the pre-analysis rack delivering position can be transported to the pre-analysis rack holding section 33 using the rack delivering portion 322. This ensures that no sample rack L is retained on the transport line 3aF.

The pre-analysis rack holding section 33 can hold a plurality of sample racks L at a time (two in the present embodiment). Therefore, the plurality of sample racks L (at most two in the present embodiment) can be left on standby at a time in the pre-analysis rack holding section 33. This further ensures that no sample rack L is retained on the transport line 3aF.

Further, the sample rack L held in the post-analysis rack holding section 34 after all of the samples therein were measured is not transported to the sample transport unit 3b, 3c or 4 in the subsequent stage but is immediately transported to the sample feed and collection device 2 by the return line 3aR. Therefore, the number of the sample racks L transported on the transport lines 3bF, 3cF and 4F can be reduced. This further ensures that no sample rack L is retained on the transport lines 3bF, 3cF and 4F.

<Other Embodiments>

In the embodiment described so far, the sample container T at the sample feeding position 35c of the measurement line 3aM, 3bM, or 3cM is fetched into the measurement unit 51, 52, or 53 so that the sample contained in the sample container T is suctioned. Alternatively, the measurement unit 51, 52, or 53 may suction the sample of the sample container T held in the sample rack L on the transport line 3aF, 3bF, or 3cF as well as the sample rack L on the measurement line 3aM, 3bM, or 3cM.

The measurement unit 51, 52, or 53 may directly suction the sample of the sample container T retained in the sample rack L on the measurement line 3aM, 3bM, or 3cM.

In the embodiment described so far, the sample transport device 3 has the sample transport units 3a, 3b, 3c, 4 which independently operate, however, the structure of the sample transport device 3 is not limited thereto. A single sample transport device having an inseparable structure may be provided on the front side of the measurement units 51, 52 and 53 and the smear preparation device 6, and the single sample transport device carries out the transport of the sample rack L to the measurement units 51, 52 and 53 and the smear preparation device 6. In the suggested structure, one transport line and one measurement line are provided in parallel with each other, and a plurality of pre-analysis (pre-process) rack holding sections (four holding sections) for holding the sample rack L transported from the transport line are provided, which respectively correspond to the measurement units 51, 52 and 53 and the smear preparation device 6.

In the embodiment described so far, the sample processing apparatus 1 is equipped with the hemocyte analyzing device 5 which classifies the hemocytes included in the sample and also counts the hemocytes based on the different types thereof. However, the structure of the sample processing apparatus 1 is not limited thereto. The sample processing apparatus may be equipped with any sample analyzing device other than the hemocyte analyzing device, such as immunoassay device, blood coagulation measuring device, biochemical analyzing device, or urine analyzing device, wherein a sample such as blood or urine is transported to a measurement unit of the sample analyzing device.

In the embodiment described so far, the hemocyte analyzing device 5 is equipped with the three measurement units 51, 52, and 53 and the information processing unit 54. However, the structure of the hemocyte analyzing device 5 is not limited thereto. Either of a single measurement unit or a plurality of measurement units may be provided, and the measurement unit and the information processing unit may be integrally formed. In place of controlling the mechanisms of the measurement units 51, 52, and 53 using the information processing unit 54, each of the measurement units may have a controller including a CPU and a memory, wherein the controllers control the measurement units, and the information processing unit processes measured data obtained by the measurement units to generate a sample analysis result.

In the embodiment described so far, each of the single computers 8a, 80a is solely responsible for all of the processing steps of the computer programs 84a, 840a, which, however, is not the only option. A distributed system may be used, wherein processing steps similar to those of the computer programs 84*a*, 840*a* are carried out by a plurality of devices (computers) in a distributed manner.

What is claimed is:

1. A rack transporting apparatus for transporting a sample rack to a sample processing unit which processes a sample, comprising:
    a first transport path configured to transport a sample rack to the sample processing unit;
    a second transport path configured to receive a sample rack holding a sample container from an upstream side of the rack transporting apparatus and transport the received sample rack toward a downstream side of the rack transporting apparatus;
    a third transport path configured to receive a sample rack from the downstream side of the rack transporting apparatus and transport the received sample rack toward the upstream side of the rack transporting apparatus;
    a first storing section that is arranged between the first transport path and the second transport path, and that has a space for storing a sample rack;
    a first rack transferring mechanism configured to transport the sample rack located on the second transport path to the first storing section, and transfer the sample rack from the first storing section to the first transport path such that a path through which the sample rack is transported from the second transport path to the first transport path passes through the first storing section and is orthogonal to the first transport path;
    a second storing section that is arranged between the first transport path and the second transport path, and that has a space for storing the sample rack;
    a second rack transferring mechanism configured to transfer the sample rack located on the first transport path to the second storing section, and to transfer the sample rack from the second storing section to both of the second transport path and the third transport path such that a path through which the sample rack is transported from the first transport path to the second and third transport paths is a single continuous path that passes through the second storing section and is orthogonal to the first transport path; and
    a controller configured to control both the first rack transferring mechanism and the second rack transferring mechanism, wherein
    when the sample processing unit is to process a sample in the sample rack located on the second transport path, the controller is programmed to control the first rack transferring mechanism so as to transfer the sample rack to the first storing section and so as to stay the sample rack in the first storing section until a transportation state of another sample rack on the first transport path meets a predetermined condition; and
    when the sample rack located on the first transport path is to be transported to the downstream side of the rack transporting apparatus, the controller is programmed to control the second rack transferring mechanism so as to transfer the sample rack to the second transport path through the second storing section, and when the sample rack located on the first transport path is to be transported to the upstream side of the rack transporting apparatus, the controller controls the second rack transferring mechanism so as to transfer the sample rack to the third transport path through the second storing section.

2. The rack transporting apparatus of claim 1, wherein each of the first and second storing sections has a space for storing a plurality of sample racks.

3. The rack transporting apparatus of claim 1, wherein the first transport path has a length for disposing thereon a plurality of sample racks.

4. The rack transporting apparatus of claim 1, wherein the first rack transferring mechanism comprises:
    a delivering section which delivers the sample rack on the second transport path to the first storing section; and
    a sending portion configured to send the sample rack stored in the first storing section to the first transport path.

5. The rack transporting apparatus of claim 1, wherein the first transport path and the second transport path are provided in parallel with each other; and
    the first rack transferring mechanism transfers the sample rack in a direction orthogonal to a transport direction by the first transport path.

6. The rack transporting apparatus of claim 5, wherein an upper surface of the second transport path and an upper surface of the first transport path form a continuous plane having a substantially equal height with the first storing section interposed therebetween; and
    the first rack transferring mechanism slides the sample rack from the second transport path to the first transport path through the first storing section.

7. The rack transporting apparatus of claim 6, wherein the first rack transferring mechanism slides the sample rack by pushing the sample rack from the second transport path to the first transport path through the first storing section.

8. The rack transporting apparatus of claim 1, wherein the second rack transferring mechanism comprises:
    a second delivering section configured to deliver the sample rack on the first transport path to the second storing section; and
    a second sending portion configured to send the sample rack stored in the second storing section to either of the second transport path and the third transport path.

9. The rack transporting apparatus of claim 1, wherein the first transport path, the second transport path, and the third transport path are provided in parallel with each other; and
    the second rack transferring mechanism transfers the sample rack in a direction orthogonal to a transport direction of the second transport path.

10. The rack transporting apparatus of claim 9, wherein an upper surface of the first transport path, an upper surface of the second transport path, and an upper surface of the third transport path form a continuous plane having a substantially equal height with the second storing section interposed therebetween; and
    the second rack transferring mechanism slides the sample rack from the first transport path to either of the second transport path and the third transport path through the second storing section.

11. The rack transporting apparatus of claim 10, wherein the second rack transferring mechanism slides the sample rack by pushing the sample rack from the first transport path to either of the second transport path and the third transport path through the second storing section.

12. The rack transporting apparatus of claim 1, wherein the controller determines whether or not it is possible to transfer the sample rack to the second transport path when transferring the sample rack disposed on the first transport path to the second transport path, and the controller controls the second rack transferring mechanism so as to stay the sample rack in the second storing section when the controller has determined that it is not possible to transfer the sample rack to the second transport path, and the controller determines whether or not it is possible to transfer the sample rack to the third transport path when transferring the sample rack disposed on the first transport path to the third transport path, and the controller controls the second rack transferring mechanism so as to stay the sample rack in the second storing section when the controller has determined that it is not possible to transfer the sample rack to the third transport path.

13. A sample processing apparatus, comprising:
a rack transport unit configured to transport a sample rack holding a sample container containing a sample;
a sample processing unit configured to process the sample in the sample rack transported by the rack transport unit; and
a controller configured to control the rack transport unit, wherein the rack transport unit comprises:
a first transport path configured to transport a sample rack to the sample processing unit;
a second transport path configured to receive a sample rack from an upstream side of the rack transport unit and transport the received sample rack toward a downstream side of the rack transport unit;
a third transport path configured to receive a sample rack from the downstream side of the rack transport unit and transport the received sample rack toward the upstream side of the rack transport unit;
a first storing section that is arranged between the first transport path and the second transport path, and that has a space for storing a sample rack;
a first rack transferring mechanism configured to transfer the sample rack located on the second transport path to the first storing section, and transfer the sample rack from the first storing section to the first transport path such that a path through which the sample rack is transported from the second transport path to the first transport path passes through the first storing section;
a second storing section that is arranged between the first transport path and the second transport path, and that has a space for storing a sample rack; and
a second rack transferring mechanism configured to transfer the sample rack located on the first transport path to the second storing section, and to transfer the sample rack from the second storing section to both of the second transport path and the third transport path such that a path through which the sample rack is transported from the first transport path to the second and third transport paths is a single continuous path that passes through the second storing section, wherein when the sample processing unit is to process the sample in the sample rack located on the second transport path, the controller is programmed to control the first rack transferring mechanism so as to transfer the sample rack to the first storing section and so as to stay the sample rack in the first storing section until a transportation state of another sample rack on the first transport path meets a predetermined condition; and when the sample rack located on the first transport path is to be transported to the downstream side of the rack transport unit, the controller is programmed to control the second rack transferring mechanism so as to transfer the sample rack to the second transport path through the second storing section, and when the sample rack located on the first transport path is to be transported to the upstream side of the rack transport unit, the controller controls the second rack transferring mechanism so as to transfer the sample rack to the third transport path through the second storing section.

14. The sample processing apparatus of claim 13, wherein each of the first and second storing sections has a space for storing a plurality of sample racks.

15. The sample processing apparatus of claim 13, wherein the first transport path has a length for disposing thereon a plurality of sample racks.

16. The sample processing apparatus of claim 13, further comprising
a second rack transport unit configured to transport a sample rack, the second rack transport unit being disposed at the downstream side of the rack transport unit; and
a second sample processing unit configured to process a sample in the sample rack transported by the second rack transport unit,
wherein the second rack transport unit comprises:
a fourth transport path configured to receive a sample rack transported from the second transport path of the rack transport unit and transport the received sample rack toward a downstream side of the second rack transport unit;
a fifth transport path configured to transport the sample rack transferred from the fourth transport path to the second sample processing unit;
a sixth transport path configured to transport a sample rack to the third transport path of the rack transport unit;
a third rack transferring mechanism configured to transfer the sample rack located on the fourth transport path to the fifth transport path through a third storing section being capable of storing the sample rack; and
a fourth rack transferring mechanism configured to transfer the sample rack located on the fifth transport path to either of the fourth transport path and the sixth transport path through a fourth storing section being capable of storing the sample rack.

17. The sample processing apparatus of claim 16, further comprising
a rack collection unit configured to collect a sample rack, the rack collection unit being disposed at the upstream side of the rack transport unit, wherein
the controller is configured to determine whether or not it is necessary to transport the sample rack disposed on the first transport path of the rack transport unit to the second rack transport unit, and controls the rack transport unit so that the sample rack is transported by the third transport path of the rack transport unit to the rack collection unit when the controller has determined that it is unnecessary to transport the sample rack to the second rack transport unit.

18. The sample processing apparatus of claim 17, wherein the sample processing unit is a hemocyte measurement unit for measuring hemocytes in blood;
the second sample processing unit is a smear preparation unit for preparing a smear by smearing the blood on a glass slide; and
the controller controls the rack transport unit so that the sample rack is transported to the second rack transport unit when it is necessary to prepare the smear, by the smear preparation unit, using the blood in the sample rack disposed on the first transport path.

19. The rack transporting apparatus of claim 1, wherein the controller controls the first rack transferring mechanism so as to stay the sample rack in the first storing section until the another sample rack has been transported to a predetermined position on the second transport path or until the another sample rack has been transported out of the second transport path.

20. The rack transporting apparatus of claim 1, wherein the second transport path is arranged between the first transport path and the third transport path.

21. The rack transporting apparatus of claim 1, further comprising:
   a first sensor configured to determine whether a sample rack is located at a rack delivering position located on the second transport path; and
   wherein the first rack transferring mechanism is configured to transport the sample rack located on the rack delivering position of the second transport path in response to a determination by the first sensor that a sample rack is located at the rack delivering position of the second transport path.

* * * * *